(12) United States Patent
Rodrigues (10) Patent No.: US 8,318,098 B2
(45) Date of Patent: Nov. 27, 2012

(54) METHOD AND APPARATUS FOR DETECTING AN ANALYTE

(75) Inventor: Rogerio Geraldes Rodrigues, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 1109 days.

(21) Appl. No.: 11/929,313

(22) Filed: Oct. 30, 2007

(65) Prior Publication Data

US 2009/0142791 A1    Jun. 4, 2009

(51) Int. Cl.
*G01N 33/53* (2006.01)
(52) U.S. Cl. ............ 422/82.01; 436/518; 436/524; 436/806; 422/50
(58) Field of Classification Search .......... 436/518, 436/524, 806; 435/7.1, 283.1, 287.1, 287.2; 422/50, 82.01
See application file for complete search history.

(56) References Cited

U.S. PATENT DOCUMENTS

| | | | | |
|---|---|---|---|---|
| 4,749,850 | A * | 6/1988 | Chemla et al. | 257/236 |
| 6,542,229 | B1 * | 4/2003 | Kalal et al. | 356/128 |
| 6,743,581 | B1 * | 6/2004 | Vo-Dinh | 435/6 |
| 2005/0253152 | A1 | 11/2005 | Klimov | |
| 2007/0052428 | A1 * | 3/2007 | Van Berkel | 324/662 |
| 2008/0064025 | A1 * | 3/2008 | Su | 435/5 |

OTHER PUBLICATIONS

Andreev; Theoretical Analysis of Optical Transitions in GaN-based Quantum Dot Structures; 2001; J3.25.1-6; vol. 642 at Materials Research Society.
Clapp; Fluorescence Resonance Energy Transfer Between Quantum Dot Donors and Dye-Labeled Protein Acceptors; 301-310; JACS Articles 2004.
Clapp; Quantum Dot-Based Multiplexed Fluorescence Resonance Energy Transfer; 18212-18221; JACS Articles 2005.
Duan; Single-Nanowire Electrically Driven Lasers; 241-254; Nature Publishing Group 2003, vol. 421.
Duan; Single-Nanowire Electrically Driven Lasers; Supplementary Materials; 4 pps; 2003.
Ji; iNgAn/gAn Multi-Quantum Dot Light-Emitting Diodes; 114-118; Journal of Crystal Growth 263 (2004).
Lichlyter; Development of a Novel FRET Immunosensor Technique; 219-226; Biosensors and Bioelectronics 19 (2003).
Selvin; The Renaissance of Fluorescence Resonance Energy Transfer; 730-734; Nature Structural Biology, vol. 7, No. 9, Sep. 2000.
Suzuki; Swing of the Lever Arm of a Myosin Motor at the Isomerization and Phosphate-release Steps; 380-383; Nature, vol. 396, No. 26, Nov. 1998.
Swanson; A Fully Multiplexed CMOS Biochip for DNA Analysis; 22-30; Sensors and Actuators B (2000).
Thrush; Integrated Bio-Fluorescence Sensor; 103-110; Journal of Chromatography, 2003.
Tsien; Seeing the Machinery of Live Cells; 5 pps.; Science, vol. 280, Issue 5371, 1954-1955, Jun. 19, 1998.
Willard; Resonant Energy-Transfer Sensor; 575-576; Nature Publishing Group 2003.

(Continued)

*Primary Examiner* — Melanie J Yu
(74) *Attorney, Agent, or Firm* — Fletcher Yoder, P.C.

(57) ABSTRACT

Embodiments of the present technique facilitate the detection of analytes. Detection is generally achieved by binding agents labeled with non-radiative energy transfer acceptors. The binding agents, when bound to a specific analyte, change conformation such that the distance between the respective non-radiative energy transfer acceptors and a respective quantum dot or quantum well changes. Certain embodiments of the present technique also comprise readout circuitry configured to determine rates of non-radiative energy transfer electrically and not optically.

8 Claims, 6 Drawing Sheets

OTHER PUBLICATIONS

Yuan; Electrically Driven Single-Photon Source; 102-105; Science, vol. 295, Jan. 4, 2002.
Medintz; Adaptable Reagentless Biosensor; S-25/Rev:Apr05.
Andrew; Energy Transfer Across a Metal Film Mediated by Surface Plasmon Polaritons; 1002-1005; Science, vol. 306, Nov. 5, 2004.
Clapp; Forster Resonance Energy Transfer Investigations Using Quantum-Dot Fluorophores; 47-57; ChemPhysChem 2006, 7.
Achormann; Energy-Transfer Pumping of Semiconductor Nanocrystals Using an Epitaxial Quantum Well; Nature Publishing Group 2004, vol. 429, No. 10, Jun. 2004.

* cited by examiner

METHOD AND APPARATUS FOR DETECTING AN ANALYTE

BACKGROUND OF THE INVENTION

The invention relates generally to analysis tools and more specifically to low abundance analyte detection and analysis.

In many analytical applications, it may be desirable to detect the presence of small amounts of a particular type of an analyte or analytes. For example, it may be desirable to detect trace amounts of a pollutant, a contaminant, a carcinogen, or other chemical in a sample, such as an environmental soil or water sample or a blood or fluid sample obtained from an organism. Similarly, various medical, industrial, and security applications may also benefit from being able to detect trace amounts of analytes, particularly in complex or mixed sample materials.

For example, detection of small numbers of particular analytes in complex solutions represents a major focus of biomedical research. However, present approaches for detecting low abundance analytes represent various challenges. Representative applications include luminescent or fluorescent methodologies that typically require either relatively high concentrations of the analyte of interest in the sample or a large number of detection molecules to generate a measurable signal. Present approaches utilize bulky and expensive equipment such as optical detection systems, laser sources, microscopes, or fluorometers.

Further, present techniques for detecting low abundance analytes may involve preparing a sample for analysis, such as to separate or concentrate the analyte to be detected or to label the analyte to facilitate detection. Preparing the samples, however, typically requires time and resources that may be scarce. In addition, the need for sample preparation and for bulky, specialized equipment generally prevents use of such analyte detection systems outside of a laboratory or in an automated, small scale setting, which might otherwise be desirable. In spite of the substantial facilities and labor required, incorrect identification of the analytes is still possible.

BRIEF DESCRIPTION OF THE INVENTION

Embodiments of the present invention address some or all of the problems noted above with regard to analyte detection. For example, problems associated with the need for bulky and expensive equipment, the need for sample preparation prior to analysis, and/or poor specificity in analyte detection are addressed by embodiments of the present invention.

In accordance with one aspect of the present technique, an analysis tool is provided. The analysis tool comprises a substrate comprising a plurality of nano-sized light emitters configured to function as energy donors of a non-radiative energy transfer process when excited by an electric field. The analysis tool also comprises one or more binding agents conjugated to each nano-sized light emitter and readout circuitry configured to determine the rate of non-radiative energy transfer between said the nano-sized light emitters and one or more non-radiative energy transfer acceptors.

In accordance with another aspect of the present technique, an analysis tool is provided. The analysis tool comprises a substrate comprising a plurality of nano-sized light emitters configured to function as energy donors of a non-radiative energy transfer process when excited by an electric field. The analysis tool also comprises a plurality of quantum dots conjugated to the substrate and one or more binding agents conjugated to each quantum dot. In addition, the analysis tool comprises readout circuitry configured to determine the rate of non-radiative energy transfer between the nano-sized light emitters and the quantum dots and/or between the quantum dots and one or more non-radiative energy transfer acceptors.

In accordance with a further aspect of the present technique, a method of detecting analytes is provided. The method includes the step of providing a substrate comprising one or more light emitter structures configured to function as energy donors of a non-radiative energy transfer process when excited by an electric field. One or more quantum dots are associated with each light emitter structure. The one or more quantum dots are conjugated to binding agents labeled with one or more non-radiative energy transfer acceptors. A first rate of non-radiative energy transfer from the quantum dots to the non-radiative energy transfer acceptors is determined. The binding agents are exposed to a sample containing one or more analytes that bind to the binding agents. When the binding agents bind to the one or more analytes, the binding agents undergo a conformational change that alters the distance between the respective non-radiative energy transfer acceptors and the respective quantum dot. A second rate of non-radiative energy transfer from the quantum dots to the non-radiative energy transfer acceptors is determined.

In accordance with a further aspect of the present technique, a method of detecting analytes is provided. The method includes the step of providing a substrate comprising one or more light emitter structures configured to function as energy donors of a non-radiative energy transfer process when excited by an electric field. The one or more light emitter structures are conjugated to binding agents labeled with one or more non-radiative energy transfer acceptors. A first rate of non-radiative energy transfer from the light emitter structures to the non-radiative energy transfer acceptors is determined. The binding agents are exposed to a sample containing one or more analytes that bind to the binding agents. When the binding agents bind to the one or more analytes, the binding agents undergo a conformational change that alters the distance between the respective non-radiative energy transfer acceptors and the respective light emitter structure. A second rate of non-radiative energy transfer from the light emitter structures to the non-radiative energy transfer acceptors is determined.

In accordance with a further aspect of the present technique, a circuit is provided. The circuit comprises a pump pathway connected to at least one light emitter. When current passes through the pump pathway, an electrical field stimulates the non-radiative transfer of energy from the light emitter to a quantum dot or to a non-radiative energy transfer acceptor. The circuit also comprises a readout pathway connected to at least one light emitter. When current passes through the readout pathway, the changes in the electrical potential attributable to the non-radiative transfer of energy to the quantum dot or to the non-radiative energy transfer acceptor are measured. In addition, the circuit comprises a switch configured to switch between the pump pathway and the readout pathway.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The present techniques are directed to the detection of analytes within a sample. In certain embodiments, the sample being analyzed may consist of blood, tissue, or environmental (soil, water, air) samples. In some embodiments, the sample is not prepared or treated (such as to separate, concentrate, or label the analyte) prior to analysis. For example, in such an implementation, a blood sample may be analyzed after withdrawal from a patient, without undergoing centrifugation or clotting reactions prior to the analysis. In addition, in certain embodiments described herein, the analysis of the sample may be performed on a substrate, such as a chip, which is portable and/or disposable. Further, in these embodiments, the substrate may incorporate circuitry that allows for electrical, as opposed to optical, readout.

To more clearly and concisely describe and point out the subject matter of the claimed invention, the following definitions are provided for specific terms, which are used in the following description and claims. The singular forms "a", "an", and "the" include plural referents unless the context clearly dictates otherwise.

As used herein, the term "analyte" refers to a particle to be detected and/or quantified within a sample. The term analytes includes, but is not limited to, simple or complex molecules (chemical units comprised of one or more atoms). Examples of such molecules include amino acids, oligo- and polypeptides, polysaccharides, lipids, hormones, DNA, and RNA. However, more generally, an analyte should be understood to be any substance that can be bound by a binding agent, as defined below.

As used herein, the term "binding agent" refers to a material capable of binding to and forming a complex with a specific analyte. Examples of binding agents include proteins or protein complexes that exhibit specific binding to target analytes. These proteins or protein complexes include, but are not limited to, antibodies, surface receptors or receptor complexes present on cellular membranes, enzymes, and artificial protein sequences.

As used herein, the term "non-radiative energy transfer" or "NRET" refers to the radiationless transmission of energy quanta between a donor, which initially absorbs the energy, and an acceptor, which receives the transferred energy. The donor may be excited to a transmissive quantum state by exposure to a particular wavelength of light or by exposure to an electrical field. Upon the transfer of the emission energy to the acceptor, the donor returns to its electronic ground state. In certain applications, the donor and the acceptor may be different sites on a molecule or molecular complex or they may be distinct and discrete molecules. In addition, synthetic quantum confined nanostructures made of semiconductor material, such as quantum wells and quantum dots, may have the capability of acting as donors and/or acceptors of non-radiative energy transfer. In either case the transfer of energy is by resonance interaction between a donor entity and an acceptor entity at a very small distance, such as 10 nanometers, from each other without conversion to optical or thermal energy and without kinetic interaction between the donor and the acceptor.

As used herein, the prefix "nano-" or reference to "nanometer" scale or dimensions is intended to encompass sizes and distances ranging from about 1 nm to about 1 μm, taking into account measurement and fabrication error terms and standard rounding conventions.

As used herein, the term "quantum well" refers to a thin layer of material within which the potential energy of an electron is less than in the adjacent layers, usually called "barrier layers". In this manner, the motion of an electron in the direction perpendicular to the plane of the quantum well layer is quantized. Typically the thickness of the layer of material comprising the quantum well is between about 1 nanometer and about 5 nanometers thick, while its length and width are unrestricted and, virtually, infinitely larger than its thickness. Examples of materials which may be used to form the quantum well and its barrier layers include compound semiconductors, such as indium gallium nitride (InGaN) and gallium nitride (GaN).

Typically, quantum well and barrier layers are produced using techniques such as metal organic chemical vapor deposition (MOCVD) or molecular beam epitaxy (MBE), which allow for a highly controlled epitaxial deposition, with accuracy down to one single atomic layer. The quantum well and barrier layers may be deposited as continuous layers extending over an entire substrate, such as a semiconductor wafer, typically about 5 centimeters to about 10 centimeters in diameter, and tending to become larger as the substrate production and the epitaxial deposition technologies evolve. These wafers, with the deposited well and barrier layers, are subsequently segmented into dice which, due to device design or due to fabrication yield reasons, may be as small as about 100×100 square microns but may also be as large about 1×1 square millimeters or larger. Within each dice, the smallest cell of an active light emitting device may be built on a "quantum well segment" defined using nanolithography and reactive ion etching techniques. In one implementation, the quantum well segments have lateral dimensions of about 10 nanometers to about 100 nanometers. In such an implementation, the small lateral dimensions provide additional electron quantum confinement, with the resulting structure behaving similarly to a quantum dot. In other embodiments, however, the quantum well segments have relatively large lateral dimensions, as large as tens to hundreds of microns, and provide no additional quantum confinement.

As used herein, the term "quantum dot" refers to a semiconductor structure of nanometer dimensions with a discrete quantized energy emission spectrum that is directly correlative to its physical size. Quantum dots may participate in non-radiative energy transfer as either an energy donor, an energy acceptor, or as an intermediate structure functioning as both an acceptor (relative to an upstream donor) and as a donor (relative to a downstream acceptor).

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties that are sought and taking into account the appropriate error terms. At the very least, each numerical parameter should at least be construed in light of the number of reported significant digits and by applying ordinary rounding techniques.

Figure 1:
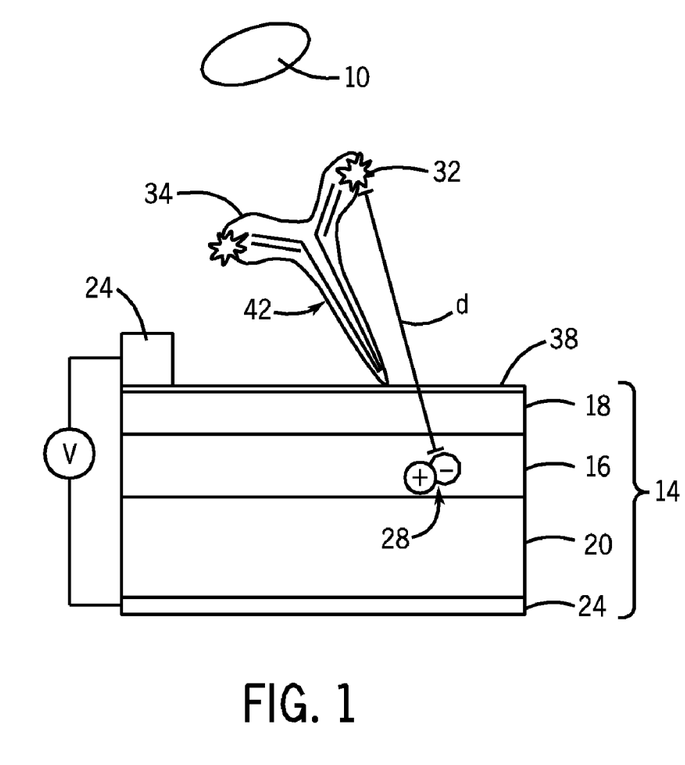
FIG. 1 is a diagrammatical view of an exemplary system for detection of an analyte, in accordance with aspects of the present technique.
Figure 2:
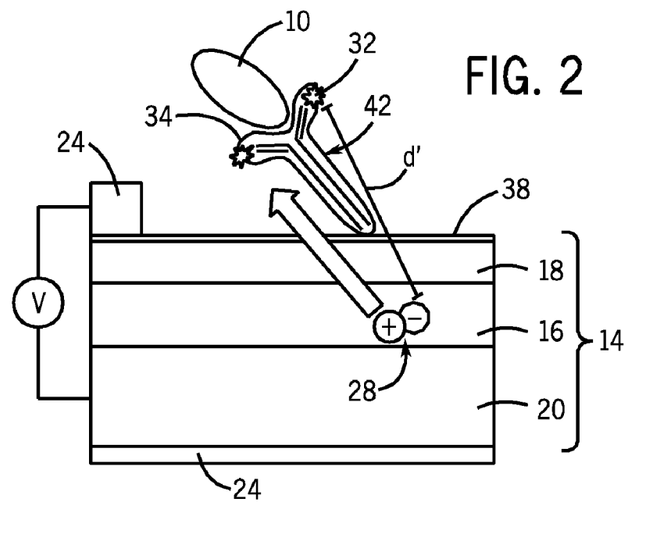
FIG. 2. is a diagrammatical view of the system of FIG. 1 bound to an analyte, in accordance with aspects of the present technique.

Turning now to FIGS. 1 and 2, an embodiment of the present technique is depicted wherein non-radiative energy transfer (NRET) processes are employed for the detection of analytes 10. In the depicted NRET process, a semiconductive substrate 14 is provided which comprises a quantum well 16. In one embodiment, the quantum well 16 is made of indium gallium nitride (InGaN) where the percentage of indium in the quantum well 16 is between about 5% and about 10%.

In the depicted example, the substrate 14 also includes a top layer 18 above the quantum well 16 and a bottom layer 20 below the quantum well 16. In certain embodiments where the quantum well 16 is uncapped, some or all of the top layer 18 may be absent. In one exemplary embodiment, the top layer 18 and the bottom layer 20 are made of gallium nitride (GaN). In certain embodiments, the top layer 18 is doped to be n-type while the bottom layer 20 is doped to be p-type, though in other embodiments this arrangement may be reversed. In one embodiment, the bottom layer 20 is between about 1 μm to about 3 μm thick; the quantum well 16 is between about 1 nm to about 5 nm thick, such as about 3 nm thick; and the top layer 18, when present, is about 2 nm to about 3 nm thick. In one embodiment, the lateral dimensions of the individual quantum well segments are in range from about 10 nm to about 1 mm.

Conductive contacts 24 are attached to the top layer 18 and the bottom layer 20. The contacts 24 allow a voltage to be applied across the substrate 14. Upon application of such a voltage, electron-hole pairs 28 are injected into the quantum well 16. The electron-hole pairs 28 injected into the quantum well 16 can non-radiatively transfer energy of a given wavelength by Förster-type dipole-dipole interactions to a suitable non-radiative energy transfer acceptor 32. Examples of such acceptors 32 include fluorescent dyes or markers. In an exemplary embodiment, for energy to be non-radiatively transferred from the quantum well 16 to the acceptor 32, the quantum well 16 and acceptor 32 are within about 10 nm from one another. The acceptor 32 is in turn excited to a higher quantum state after absorption of the non-radiatively transferred energy form the quantum well 16 and, in an exemplary embodiment, in turn emits energy at a characteristic wavelength when reverting to its original quantum state.

In the depicted embodiment of FIGS. 1 and 2, the NRET acceptors 32 are conjugated to binding agents 34, such as the depicted antibody, which bind with specificity to the analyte 10. The binding agents 34 are, in turn, conjugated to the substrate 14. In one embodiment, the surface of the substrate 14 is functionalized to facilitate attachment of the binding agents 34 to the substrate 14. For example, the substrate 14 may be functionalized by exposing the substrate 14 to a silane to form a self-assembled monolayer 38 on the top layer 18 if present or on the quantum well 16 in the absence of a top layer 18. In this exemplary embodiment, amino, hydroxyl, or thiol groups present on the binding agent 34 form covalent bonds with the monolayer 38 of silane, thereby attaching the binding agent 34 to the substrate 14.

In one embodiment of the present technique, the binding agent 34 comprises an antibody or other proteinaceous receptor whose conformation is altered when binding the analyte 10. For example, in FIG. 1, the binding agent 34 is not bound to an analyte 10 and the acceptors 32 bound to the binding agent 34 are at respective distances "d" from the quantum well 16. As depicted in FIG. 2, however, the binding of the analyte 10 and the binding agent 34 results in a conformation change in the binding agent 34 such that the acceptor 32 and the quantum well 16 are now separated by distance "d". For example, in an embodiment where the binding agent 34 is an antibody, the antibody employed may have a g-type tail 42 that undergoes a steric change in conformation when the analyte 10 is bound, thereby changing the distance from the acceptor 32 to the quantum well 16 from d to d'. In one embodiment, the distance d is greater than about 10 nm while the distance d' is less than about 10 nm. In an alternative embodiment, the distance d is less than about 10 nm while the distance d' is greater than about 10 nm.

The preceding provides a general discussion of exemplary conformational changes that can occur when an antibody specifically binds to a target molecule. Examples of such conformational changes may take various forms. In one example, sensors for the detection of human cardiac troponins (T or I) may be used in the diagnosis of myocardial infarction. The sensors detect a conformational change observed in anti-human cardiac troponin (T or I) antibodies upon binding of the antibodies to the respective troponins. Assays based on NRET have been developed for antibodies in solution and also for antibodies immobilized on the silanized surface of an optical fiber. In techniques employing surface immobilization, only a moderate degradation of the limits of detection, from 27 nanomolar to 75 nanomolar and from 27 nanomolar to 94 nanomolar respectively, has been observed. Also, attesting to the generality of the technique, comparable assays have been developed for several generic antibody-antigen pairs and similar results have been obtained. In one exemplary embodiment, in reference to FIG. 1 and FIG. 2, anti-human cardiac troponin may be employed as the binding agent 34, and human cardiac troponin may be the analyte 10. In such an embodiment, commercially available Alexa Fluor 594 may be employed as the acceptor 32, and Alexa Fluor 546 may be employed as the donor, thereby providing a functionality similar to that of the quantum well 16.

In another example of the use of NRET in the presence of protein conformational change, the conformation of the protein calmodulin changes upon peptide binding in the presence of calcium and the degree of this conformation change can be measured using NRET. For example, in one embodiment, BODIPYFL aminophenilalanine and BODIPY558 aminophenilalanine are small fluorescent markers that can be introduced into calmodulin without significantly interfering with its structure. In such an embodiment, BODIPY558 can be introduced as an NRET acceptor into the N terminus of calmodulin and BODIPYFL can be selectively introduced as an NRET donor into one of seven different positions (Phe19, Gly40, Gly59, Leu69, Phe99, Leu112, and Gly113) within the calmodulin in addition to its C terminus, thereby creating a range of donor/acceptor distances. In this manner, different sensitivities of the NRET signal in view of the conformational change may be obtained, with the largest change of about 70% acceptor/donor fluorescence intensity ratio obtained when the acceptor is at position Gly40 and with other positions resulting in smaller sensitivities proportional to their respective positions. For the Gly40 position, NRET measurements yield acceptor/donor distances d of 43.4 Å and d' of 49.6 Å, comparable to those obtained from Nuclear Magnetic Resonance (NMR) data. Not all acceptor positions lead to the expected changes in the NRET signal, suggesting that effects such as orientation and position of the fluorophores may be a factor. Therefore, when predicting performance of a conformation change sensor based on NRET measurements, the particular molecular system may need to be studied. Further, in certain embodiments, time-resolved measurement techniques may be employed to obtain a finer resolution in the measurement of distances. Turning to FIG. 1 and FIG. 2 again, in accordance with the present example calmodulin may be employed as the binding agent 34, calmodulin-binding peptide may be the analyte 10, BODIPY558 may be employed as the acceptor 32, and BODIPYFL may be employed as the donor, thereby providing a functionality similar to that of the quantum well 16.

In another example, conformational changes of glucose-binding protein (GBP) may be detected using NRET to produce sensitive and specific glucose sensors. In this example, fluorescent reporter groups are incorporated into GBP in such a manner that the spatial separation between these fluorescent moieties changes when glucose binds, thus generating a signal that can be detected optically. Native GBP has a high binding affinity to glucose. In its structure, both the N-terminal and C-terminal domains are composed of a core of β sheets flanked by two layers of α helices. A cleft between the two domains has been identified as the binding site for glucose. When glucose binds to GBP, the GBP undergoes a conformational change, resulting in an alteration of the distance between the C-terminal and N-terminal domains. In this embodiment, to achieve a measurable signal when glucose binds to GBP, fluorescent reporter proteins, GFP and YFP, are fused to GBP, one to each end of GBP, in such a manner that the spatial separation between the fluorescent moieties changes when the ligand binds. The diameter of GBP is 50 Å, providing a separation between the two reporter proteins that allows the fluorescence energy transfer technique to be used for glucose measurement. GFP and YFP themselves have dimensions of about 30 Å by 40 Å. The amino acid sequences of the boundary region between fusion proteins have been determined empirically to achieve a correct and stable folding of the fusion protein, which has been termed a glucose indicator protein (GIP).

Therefore, in this embodiment, the GIP fusion protein has four domains. The central two domains (of GBP) involve the glucose-binding region that undergoes a change in conformation on glucose binding. The other two peripheral domains are the added fluorescent proteins GFP and YFP. In one such an implementation, GFP, fused to the C terminus of GBP, serves as a donor to transfer the fluorescence energy to the receptor YFP fused to the N terminus of GBP. In this example, GFP has a maximum excitation wavelength at 395 nm and a maximum emission wavelength at 510 nm, whereas YFP has a maxima excitation wavelength at 513 nm and a maximum emission wavelength at 527 nm. Thus, a high-energy transfer efficiency is achieved as a result of the large spectral overlap between the emission spectra of GFPuv and the absorption spectra of YFP. When glucose binds to the GIP fusion protein, rearrangement of the flap region located on one side of the hinge β sheet of GBP occurs. The change in conformation of GBP moiety upon the binding of glucose, in turn, alters the relative position of GFPuv (donor) and YFP (acceptor), resulting in increased separation and reduction of FRET. In one such example, a 20% reduction in fluorescence due to the fluorescence resonance energy transfer may be measured as a result of glucose binding. Referring once again to FIG. 1 and FIG. 2, in this example GBP may be employed as the binding agents 34, glucose may be the analyte 10, YFP may be employed as the acceptor 32, and GFPuv may be employed as the donor, thereby providing a functionality similar to that of the quantum well 16.

With the preceding examples in mind, the change in distance between the acceptor 32 and the quantum well 16 in the presence of the analyte 10 results in a corresponding change in the rate of non-radiative energy transfer between the quantum well 16 and the acceptor 32. For example, if the distance between the quantum well 16 and the acceptor 32 decreases (d'<d) in the presence of the analyte 10, the rate of non-radiative energy transfer from the quantum well 16 to an acceptor 32 will increase. Conversely, if the distance between the quantum well 16 and the acceptor 32 increases (d'>d) in the presence of the analyte 10, the rate of non-radiative energy transfer from the quantum well 16 to an acceptor 32 will decrease. In certain embodiments, the change in distance between the quantum well 16 and the acceptor 32 due to a conformational change of the binding agent 34 in the presence of the analyte 10 may be reproducible and a monotonic function of the concentration of the analyte 10. In such embodiments, non-radiative energy transfer rate between the quantum well 16 and the acceptor 32 may be indicative of the occurrence and frequency of binding events between the binding agent 34 and the analyte 10. In particular, the degree of change in non-radiative energy transfer rates between the quantum well 16 and the acceptors 32 before and after exposure to a sample undergoing analysis may correspond to the concentration of the analyte 10 in the sample.

Figure 3:
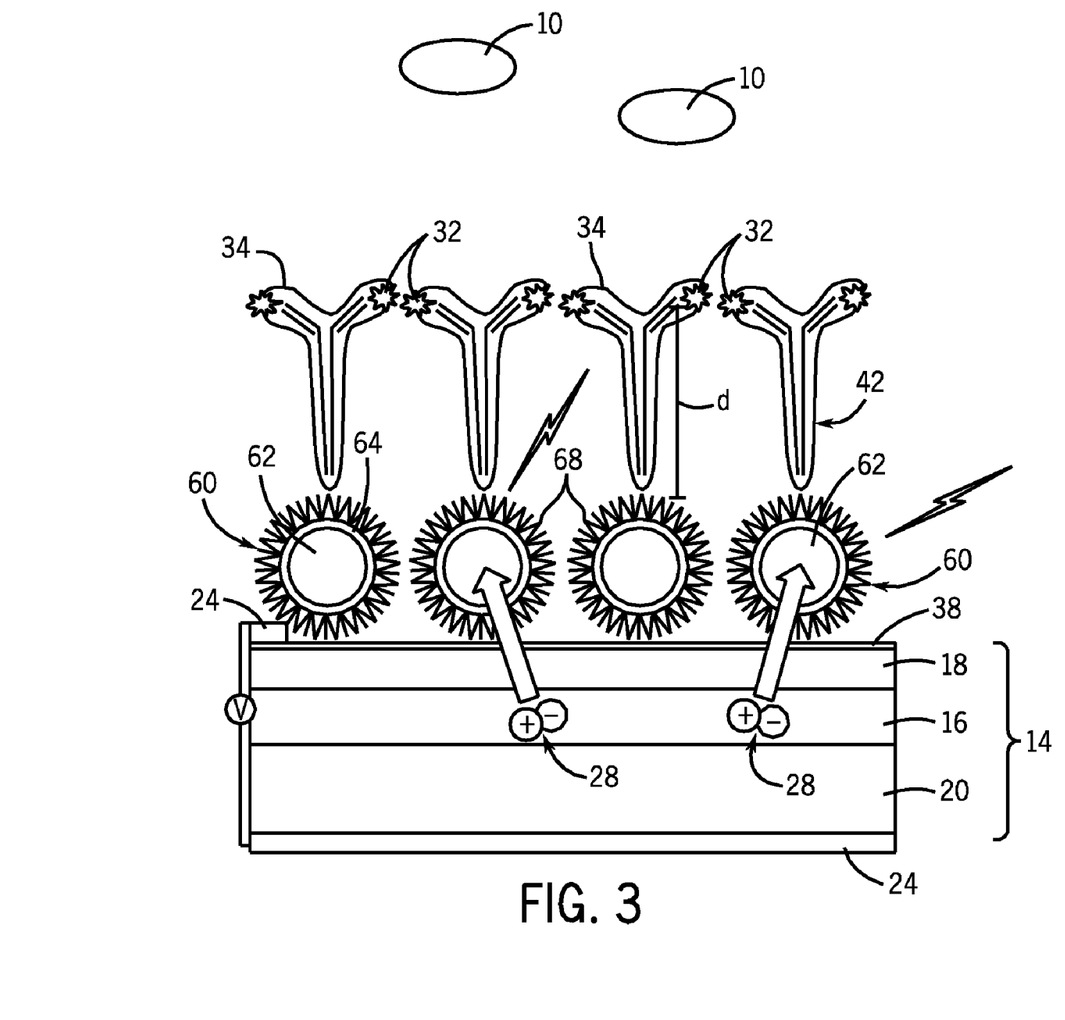
FIG. 3 is a diagrammatical view of another exemplary system for detection of an analyte, in accordance with aspects of the present technique.
Figure 4:
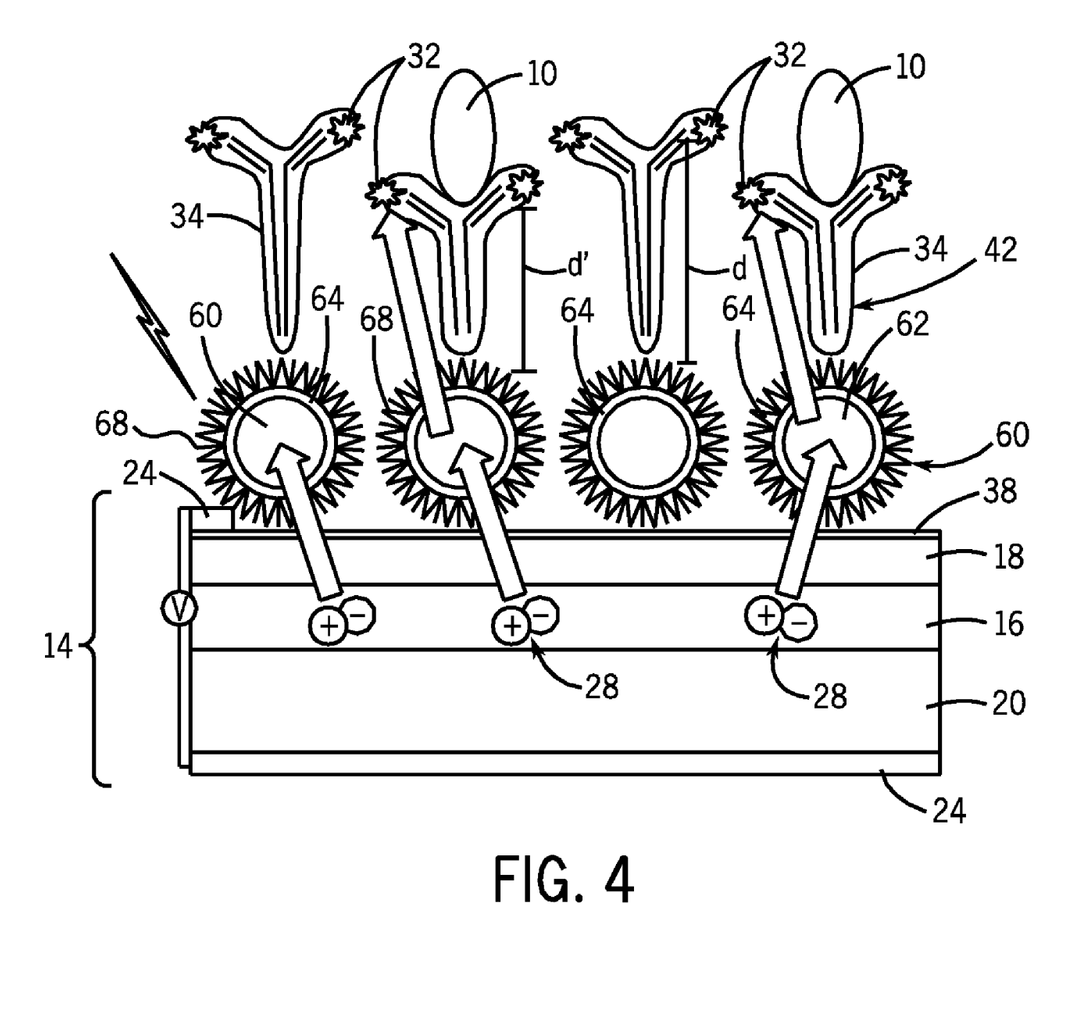
FIG. 4 is a diagrammatical view of the system of FIG. 3 bound to an analyte, in accordance with aspects of the present technique.

While FIGS. 1 and 2 depict exemplary embodiments in which a binding agent 34 is attached to the semiconducting substrate 14, FIGS. 3 and 4 depict implementations of the present technique in which quantum dots 60 are employed as an intermediary structure. For example, in one embodiment, the quantum dots 60 are assembled on the substrate 14 as a mono-layer of highly monodisperse nanocrystals using the Langmuir-Blodgett technique. In one embodiment, the quantum dots 60 comprise a core 62 of cadmium selenide (CdSe). Other exemplary quantum dot core 62 compositions include CdS, CdTe, ZnS, ZnSe, ZnTe, HgS, HgSe, HgTe, AlN, AlS, AlP, AlAs, AlSb, PbS, PbSe, PbTe, GaAs, GaN, GaP, GaSb, InAs, InN, InP, InSb, TlAs, TlN, TlP, TlSb, ZnCdSe, InGaN, InGaAs, InGaP, AlInN, InAlP, InAlAs, AlGaAs, AlGaP, AlInGaAs, AlInGaN, or combinations of these or other suitable semiconductive materials. In certain embodiments, the core 62 may have a radius between about 1 nm to about 6.5 nm, such as about 1.9 nm or about 2.0 nm.

In some, but not all, embodiments, the quantum dots 60 may also comprise one or more semiconductive coatings 64 different than the semiconductor material forming the core 62. In one embodiment, the coating 64 is a layer of zinc sulfide (ZnS). Other exemplary quantum dot coating 64 compositions include CdS, CdSe, CdTe, ZnSe, ZnTe, HgS, HgSe, HgTe, AlN, AlP, AlAs, AlSb, GaAs, GaN, GaP, GaSb, InAs, InN, InP, InSb, TlAs, TlN, TlP, TlSb, PbS, PbSe, PbTe, ZnCdSe, InGaN, InGaAs, InGaP, AlInN, InAlP, InAlAs, AlGaAs, AlGaP, AlInGaAs, AlInGaN, or combinations of these or other suitable semiconductive materials. In certain embodiments, the coating 64 may have a thickness between about 0.3 nm to about 0.9 nm, such as about 0.5 nm or about 0.6 nm. In addition, in certain embodiments the quantum dots 60 may have an outer layer 68 of organic molecules, such as trioctylphosphine and/or trioctylphosphine oxide.

In the depicted embodiment, the quantum dots 60 are attached to a substrate 14 that is capped with a top layer 18 and a monolayer 38, such as a monolayer of silane. As discussed with regard to FIGS. 1 and 2 however, in some embodiments the top layer 18 may not be present and the quantum dots 60 may instead be attached directly to the quantum well 16 or to a monolayer 38 disposed on the quantum well 16 in the absence of the top layer 18.

In the depicted embodiment of FIGS. 3 and 4, the binding agents 34 are conjugated to the quantum dots 60 as opposed to the substrate 14. For example, in embodiments where the binding agents 34 are antibodies, the tails of the antibodies may be covalently bonded to an outer layer 68 of the quantum dots 60, such as the trioctylphosphine and/or trioctylphosphine oxide outer layers noted above.

The quantum dots 60 in these embodiments act as intermediary structures that function, in a ground state, as a non-radiative energy transfer acceptor relative to quantum well 16 and, in an excited state, as a non-radiative energy transfer donor relative to acceptors 32 conjugated to the binding agents 34. For example, in the depicted embodiment, the quantum well 16 may be electrically or optically excited to a higher quantum state such that, on return to the original quantum state, the quantum well 16 non-radiatively transfers energy to respective quantum dots 60 (acting as energy acceptors). The quantum dots 60 in turn are stimulated to a higher quantum state and, upon return to their original state, non-radiatively transfer energy to a downstream acceptor 32 so that, via the emission spectrum of the quantum dot 60, the acceptor 32 is non-radiatively excited.

In one embodiment of the present technique, the binding agent 34 comprises an antibody or other proteinaceous receptor that undergoes a steric change in conformation when bound to the analyte 10. For example, in FIG. 3, the binding agent 34 is not bound to an analyte 10 and the acceptors 32 bound to the binding agent 34 are at respective distances "d" from the quantum dot 60. As depicted in FIG. 4, however, the binding of the analyte 10 and the binding agent 34 results in a conformation change in the binding agent 34 such that the acceptor 32 and the quantum dot 60 are now separated by distance "d'". For example, in an embodiment where the binding agent 34 is an antibody, the antibody employed may have a g-type tail 42 attached to the outer layer 68 of the quantum dot 60. In this embodiment, the tail 42 may undergo an allosteric change in conformation when the analyte 10 is bound, thereby changing the distance from the acceptor 32 to the quantum dot 60 from d to d'.

As depicted in FIG. 4, a change in the distance between the acceptor 32 and the quantum dot 60 in the presence of the analyte 10 results in a corresponding change in the rate of non-radiative energy transfer between the quantum dot 60 and the acceptor 32. If the distance between the quantum dot 60 and the acceptor 32 decreases (d'<d) in the presence of the analyte 10, the rate of non-radiative energy transfer from the quantum dot 60 to an acceptor 32 will increase. Conversely, if the distance between the quantum dot 60 and the acceptor 32 increases (d'>d) in the presence of the analyte 10, the rate of non-radiative energy transfer from the quantum dot 60 to an acceptor 32 will decrease. In certain embodiments, the change in distance between the quantum dot 60 and the acceptor 32 due to a conformational change of the binding agent 34 in the presence of the analyte 10 may be reproducible and a monotonic function of the concentration of the analyte 10. In such embodiments, non-radiative energy transfer rate between the quantum dot 60 and the acceptor 32 may be indicative of the occurrence and frequency of binding events between the binding agent 34 and the analyte 10. In particular, the degree of change in non-radiative energy transfer rates between the quantum dot 60 and the acceptors 32 before and after exposure to a sample undergoing analysis may correspond to the concentration of the analyte 10 in the sample.

Figure 5:
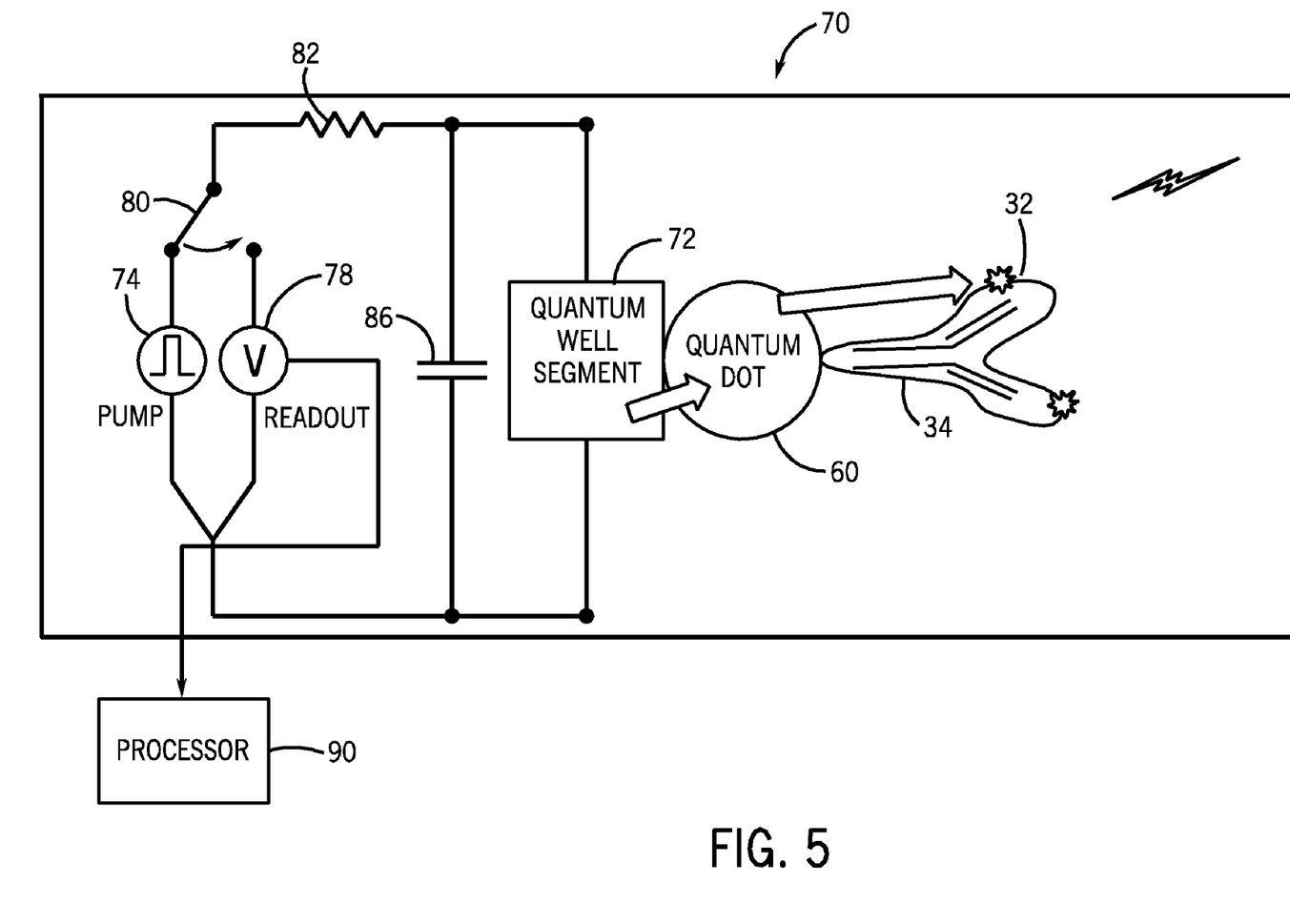
FIG. 5 is diagrammatical representation of an exemplary electrical circuit for detecting an analyte, in accordance with aspects of the present technique.

The preceding depicted embodiments relate to different mechanisms of non-radiatively transferring energy from a quantum well 16 to a final non-radiative energy transfer acceptor 32, with or without an intermediary structure such as a quantum dot 60. Turning now to FIG. 5, an exemplary circuit diagram 70 is depicted for implementing electrical, as opposed to optical, stimulation and/or readout of a non-radiative energy transfer system in accordance with the present technique. In the depicted implementation, non-radiative energy transfer from a quantum well segment 72 to an acceptor 32 via an intermediary quantum dot 60 is depicted. In other embodiments where a binding agent 34 is attached to the quantum well segment 72 (or to a substrate 14 including the quantum well segment 72) instead of a quantum dot 60, the quantum dot 60 seen on FIG. 5 may not be present. The initial excitation of the quantum well segment 72 may be initiated via electrical circuitry 70, such as by generation of an electrical field by the electrical circuitry 70. In one embodiment, the electrical circuitry 70 may include electrical pump pathway 74 and electrical readout pathway 78 which may be alternated between via switch 80. In this manner, the circuitry 70 can be alternated between applying an electrical signal to stimulate the quantum well segment 72, and possibly also the quantum dot 60, to act as non-radiative energy transfer donors, and between reading out changes in the electrical potential at the terminals of the quantum well segment 72 that may be indications of non-radiative energy transfer events. In order to achieve this functionality, the circuit 70 may be configured to count single electrons and/or to sample input signals at a very high rate, such as one Gigasample per second. As depicted, the electrical circuitry 70 may also include one or more resistance mechanisms 82, capacitors 86, or other electrical elements that are deliberately or parasitically present in circuitry.

In one embodiment, the rate of energy transfer from the quantum well 16 to the quantum dot 60 or from the quantum well segment 72 to the acceptor 32 may be measured electrically by the readout pathway 78 of the circuitry 70. Such electrical measurement may include, among others, measuring the change and/or the rate of change of energy state of the quantum well segment 72 upon non-radiative energy transfer. In such embodiments, the electrical measurement may be independent from the excited acceptor's energy emission and therefore may not require light or fluorescent detection equipment, subsequently increasing sensitivity and miniaturization capabilities. In certain implementations, the electrical circuitry 70 may be associated with a processor 90 that may acquire and analyze the data generated by the circuitry 70, such as data related to changes in energy state of the quantum well segment 72, the quantum dots 60, and/or the acceptor 32. In exemplary embodiments, the electrical circuitry 70 may be provided for use in a portable system, such as a handheld system or other easily transportable system.

In addition, the sensor can be designed such as to allow readout by optical, as opposed to electrical, techniques. In this way, the energy states and energy change rates of the donor quantum well segment 72, the acceptor 32, and possibly also an intermediate acceptor/donor quantum dot 60 all become accessible. In one embodiment, this mode of readout can be implemented using standard laboratory equipment, such as photon detectors, lenses, and filters/spectrometers. In other embodiments, these optical readout devices can be integrated with the quantum well substrate. In such embodiments, the excitation may still be achieved using electrical pulses delivered to individual quantum well segments 72. These electrical pulses may be synchronized with the signals received from the optical detectors. In such implementations, the sensor still benefits from the high spatial resolution and small required analyte volume made possible by the small lateral dimensions of the quantum well segments 72.

Figure 6:
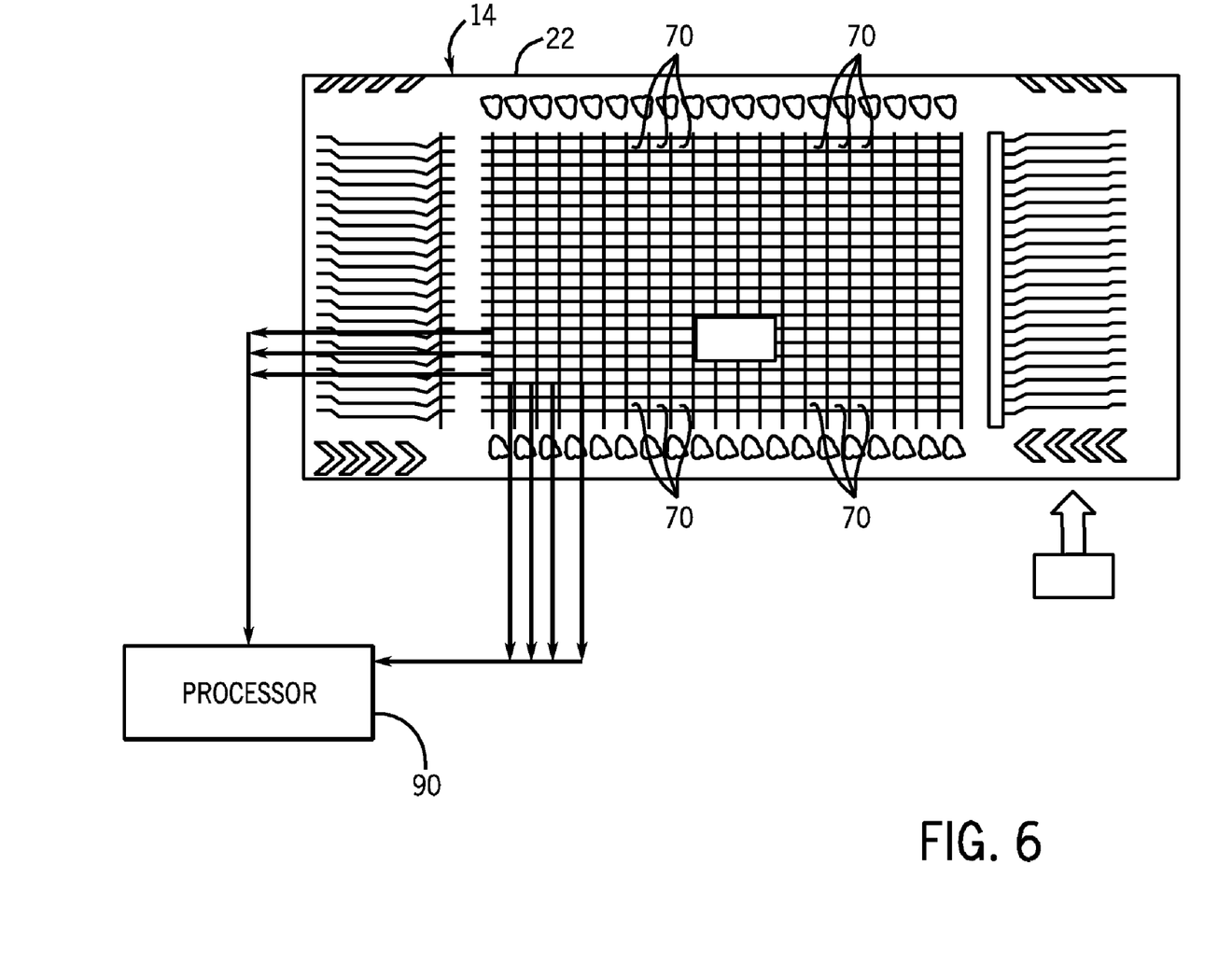
FIG. 6 is a diagrammatic representation of an exemplary system for simultaneous detection of analytes, in accordance with the present technique.

Turning now to FIG. 6, a plurality of the circuits 70, as described with regard to FIG. 5, are provided in a grid-like arrangement on a substrate such a gallium nitride semiconducting substrate 14. In one such implementation, the quantum wells segments 72 of the respective circuits 70 may be electrically isolated from one another. Each respective circuit 70 may include quantum well segments 72 (and, possibly, also quantum dots 60) conjugated to binding agents 34 specific to the same or different analytes 10, thereby creating a detection array for one or more analytes 10. As described above, the binding agents 34 may be further modified by conjugation to an acceptor 32, such as a fluorescent dye, that is excitable at a defined wavelength of optical energy and which may serve as a non-radiative energy transfer acceptor 32 relative to one or both of the quantum well segments 72 or the quantum dots 60. In one embodiment, each quantum well segment 72 and/or quantum dot 60 may be connected to independent electrical pumping and/or readout pathways 74, 78 of the respective electrical circuitry 70.

In an exemplary implementation, the substrate 14 may be manufactured as a chip suitable for use within or outside of a laboratory or clinical environment. For example, the chip may be suitable for use in a portable analyte detection instrument that may be used at or near the site where a sample is collected. Such an instrument may allow for the replacement or substitution of different chips within the instrument or may be a disposable, single use instrument. In one embodiment, the substrate 14, whether provided as a chip or in another form, may be formed using conventional lithographic or other semiconductor processing techniques.

The substrate 14, when provided with multiple circuits 70 as depicted in FIG. 6, may be used to detect one or more analytes within a sample with only one exposure protocol. In such embodiments, the various circuitries 70 provided on the substrate 14 may, individually or collectively, incorporate or be connected to a processor 90 for acquisition of electrically detected energy transfer rates and may correlate these rates to, among other things, concentrations of various analytes 10 within a sample.

Figure 7:
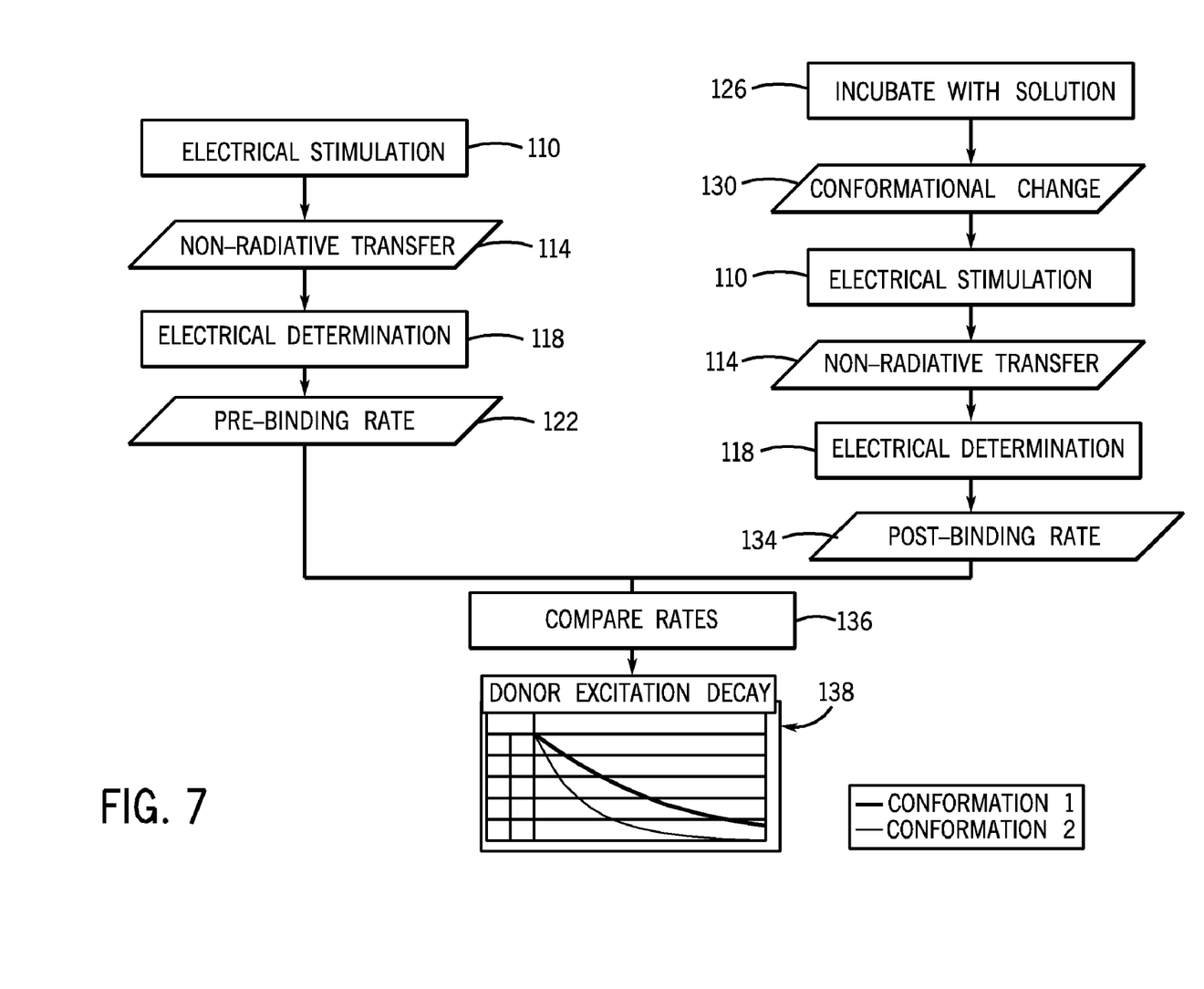
FIG. 7 is a flow chart depicting steps of detecting an analyte within a complex solution, in accordance with the present technique.

For example, turning now to FIG. 7, an exemplary process of the present technique is depicted wherein electrical stimulation (block 110) of a quantum well 16 via the pump pathway 74 of electrical circuitry 70 may result in non-radiative energy transfer 114 between the quantum well 16 and an acceptor 32, with or without an intermediary quantum dot 60. For example, in one embodiment, energy from a stimulated quantum well 16 may be non-radiatively transferred to a quantum dot 60, which is in turn stimulated to non-radiatively transfer energy to an acceptor 32. As described above, in some embodiments, the acceptor 32 is conjugated to a binding agent 34, such as an antibody, which may undergo a steric conformational change when bound to an analyte 10. Alternatively, in embodiments where no quantum dot 60 is present, the quantum well 16 may non-radiatively transfer energy directly to the acceptor 32 conjugated to the binding agent 34.

The electrical circuitry 70 may, in alternation with the stimulation of the quantum well 16, measure (block 118) changes in the energy state of one or more of the quantum well 16, the quantum dots 16 (if present), and/or the acceptor 32. These measured changes in the energy state correspond to non-radiative transfers of energy between the quantum well 16, acceptor 32, and/or the quantum dots 60. Prior to the introduction of analyte 10 to the measured system, these measured changes correspond to a pre-binding rate 122 of non-radiative energy transfer.

Following the determination of the pre-binding rate 122, the binding agents 34 may be exposed (block 126) to a sample being analyzed for the presence of an analyte 10. In the presence of the analyte 10 within the sample, binding between the binding agents 34 and the corresponding analyte 10 results in a conformational change 130 of the binding agent 34, changing the distance between the quantum well 16 or quantum dot 60 and the acceptor 32. The quantum well 16 may be electrically stimulated (block 110), such as via pump pathway 74 of the circuitry 70, to induce non-radiative energy transfer 114 between the quantum well 16 and the acceptor 32, with a quantum dot intermediary being present in some, but not all, embodiments.

Due to the conformational change 130 of the binding agent 34, the change in distance between the quantum well 16 or the quantum dot 60 and the acceptor 32 may be detectable as a change in the rate of non-radiative energy transfer. This post-binding rate 134 may be measured (block 118) electrically, such as via the readout pathway 78 of the circuitry 70.

Conceptually the pre-binding rate 122 and the post-binding rate 134 represent the speed with which energy leaves an energy donor, such as the quantum well 16 or the quantum dot 60, to excite an acceptor 32. Comparisons 138 between the pre-binding rate 122 and the post-binding rate 134 may be made (block 136) by the processor 90 to determine whether the analyte 10 is present in the sample being analyzed and, if present, to quantify the amount of analyte 10 in the sample.

In addition, the analyte-specificity of most biosensors available today is limited, especially when analyzing "dirty" or unprepared samples. Non-specific binding events can be minimized using a number of methods, but if non-specific binding events occur, they affect the sensor response in the same manner a specific binding event does. The present embodiments allow for a technique that is capable of discriminating between specific and non-specific binding events by allowing measurement of the magnitude of the associated molecular conformational change, along with the width of its distribution (measured, for example, by the standard deviation). If measurements are conducted over many sensor cells that have all been functionalized with the same capture molecule and are all exposed to the same analyte, then specific antigen-antibody binding may produce conformational changes that are distinctively larger and exhibit a narrower size distribution when compared to non-specific binding events. In accordance with the measurement techniques described herein, the statistical analysis of the NRET signal and of the corresponding molecular conformational changes may be implemented and may, thereby allow for high analyte specificity sensing.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. An analysis tool, comprising:
a substrate comprising a plurality of nano-sized light emitters configured to function as energy donors of a non-radiative energy transfer process when excited by an electric field;

one or more binding agents conjugated to each nano-sized light emitter, wherein each of the binding agents is labeled with one or more non-radiative energy transfer acceptors; and readout circuitry that determines the rate of non-radiative energy transfer between the nano-sized light emitters and the non-radiative energy transfer acceptors free of input of an optical signal.

2. The analysis tool of claim 1, wherein the plurality of nano-sized light emitters comprise quantum wells.

3. The analysis tool of claim 1, wherein the one or more binding agents comprise antibodies that undergo a change in conformation when bound to a specific analyte such that the distance between the respective non-radiative energy transfer acceptor and the respective nano-sized light emitter changes.

4. The analysis tool of claim 1, wherein the one or more binding agents have at least a first conformation in the presence of an analyte and a second conformation in the absence of the analyte and wherein non-radiative energy transfer takes place between the nano-sized light emitters and the non-radiative energy transfer acceptors at a different rate for the first and second conformations.

5. The analysis tool of claim 1, comprising electrical pumping circuitry configured to generate an electrical field.

6. The analysis tool of claim 1, wherein the readout circuitry is configured to measure electrical potentials.

7. The analysis tool of claim 1, wherein the one or more binding agents bind to at least one specific analyte.

8. The analysis tool of claim 1, wherein the readout circuitry detects a transfer of electrons to determine the rate of non-radiative transfer between the nano-sized light emitters and the non-radiative energy transfer acceptors.

* * * * *